United States Patent
Homan

(10) Patent No.: US 6,596,324 B1
(45) Date of Patent: Jul. 22, 2003

(54) SOIL CONDITIONER AND SLOW RELEASE BIO-PESTICIDAL AND FERTILIZER COMPOSITION

(76) Inventor: Joe Homan, 39/3 Nedungulam, Royapuram, Shalovandan, Madurai, Tamil Nadu (IN), 625 214

( * ) Notice: Subject to any disclaimer, the term of this patent is extended or adjusted under 35 U.S.C. 154(b) by 0 days.

(21) Appl. No.: 09/937,681
(22) PCT Filed: Feb. 4, 2000
(86) PCT No.: PCT/IN00/00010
§ 371 (c)(1), (2), (4) Date: Sep. 28, 2001
(87) PCT Pub. No.: WO01/57156
PCT Pub. Date: Aug. 9, 2001

(51) Int. Cl.$^7$ .......................... A01N 65/00; A61K 35/78
(52) U.S. Cl. ....................................... 424/761
(58) Field of Search ......................... 424/761

(56) References Cited

PUBLICATIONS

Joseph et al, Effect of coirpith on biometrical and yield parameters of Vigna, 1996, J. Phytological Res., vol. 9 No. 2, pp. 151–154.*

R. Joseph et al., "Effect of coirpith on the biometrical and yield parameters of Vigna unguiculata L. Walp and Glycine max L. in black soil", Journal of Phytological Research, vol. 9, No. 2, pp. 151–154, (abstract) CABA [online], [retrieved on Jul. 28, 2000]. Retrieved from: STN International Karlsruhe (DE); CABA Accession No.: 1998:164897; See CABA Abstract.

R. Joseph et al., "Biometrics and Yield Parameters of Greengram (Vigna radiata L.) as influence by coir waste", Journal of Phytological Research, vol. 9, No. 2, pp. 167–168, (abstract) CABA [online], [retrieved on Jul. 28, 2000]. Retrieved from: STN International Karlsruhe (DE), CABA Accession No.: 1998:164899; See CABA abstract.

V.K. Moorthy et al., "Effect of Compost on Growth of Cardamom", Water and Nutrient Management fofr Sustainable Production and Quality of Spices:Proceedings of the National Seminar, Madikeri,, Karnataka, Indiana, Oct. 5–6, 1997, 1998, pp. 85–88 (abstract) CABA [online] [retrieved on Jul. 28, 2000] Retrieved from STN International Karlsruhe (DE), CABA Accession No. 1999:5284; See CABA abstract.

* cited by examiner

Primary Examiner—Alton N. Pryor
(74) Attorney, Agent, or Firm—Baker & Daniels

(57) ABSTRACT

This invention relates to a soil conditioner, slow release bio pesticide and bio fertilizer composition. This is produced by admixing coir pith having 20% moisture with powdered neem cake upto 20% by its weight. The mixture is compressed and shaped as desired. The high rate of absorbency and slow decomposing property of coir pith enhances the slow release of bio-fertilizers and pesticides into the soil. The micro sponges of the coir pith absorbs about 900 times its volume of water during rainy season which is released slowly during dry conditions along with the decomposed products.

3 Claims, No Drawings

SOIL CONDITIONER AND SLOW RELEASE BIO-PESTICIDAL AND FERTILIZER COMPOSITION

This Application is a 371 of PCT/IN00/00010 filed Feb. 4, 2000.

TECHNICAL FIELD:

This invention relates to a soil conditioner and slow release bio-pesticidal and fertilizer composition.

In the coir industry, coconut husk is subjected to decomposition by submerging them in water. This softens up the vegetable matter inside the husk from which fibre is extracted for the production of coir and coir articles. Coir pith is a by-product obtained during this fibre processing step from coconut husk. This pith decomposes very slowly over a period of at least 10 years. In the coconut growing and coir processing areas spread through out coastal India, disposal of coir pith has been posing environmental problems. Dumping of this polluting waste product, though declared illegal in many States of India, continues, posing problems of disposal particularly because it is resistant to burning and burns for a long time, taking up atmospheric oxygen and releasing carbon dioxide. This further complicates the already existing, ecological and environmental problems.

Peat is the name given to layers of dead vegetation in varying degrees of decomposition. They are formed by the accumulation of the remains of marshy vegetation in swampy hollows in cold and temperate regions. Geologically peat is considered as the youngest member of the coal family. Peat is widely used as a fuel and is therefore becoming scarce.

Coir pith is a homogenous material composed of millions of micro sponges exhibiting capillary action and it can absorb and hold as much as 900 percentage of its weight in water. Coir pith is composed of carbon and nitrogen in the ratio of approximately 110 to 1 and has a protective lignin coating. Because of these properties, the world's fragile ecology may be saved with the help of coir pith.

BACKGROUND ART

A soil conditioner absorbs and retains moisture and releases it to the soil surrounding it when the equilibrium of water content in the soil and the conditioner is disturbed. When the soil becomes dry or less moist the conditioner having absorbed water releases it slowly to the soil around it.

DISCLOSURE OF THE INVENTION

The object of this invention is to produce a soil conditioner having a slow release bio-pesticide and bio-fertilizer which is eco-friendly and renewable. Coir pith having very high absorbency rate is ideally suited as water absorbent and storage material during the rainy season for subsequent release of water. The inventor has found that the slow rate of decomposition of coir pith makes it an ideal conditioner for subterranean soil. This, properly coupled with the ability to release moisture slowly, enables processed coir pith and neem cake combination to function as a slow release bio-pesticidal/fertilizer and soil conditioner combination. This composition surprisingly exhibits properties substantially different from either coir pith or neem cake alone. The composition absorbs and holds rain water during rainy season and when subjected to subsoil microbial action, slow decomposition of coir pith and neem cake starts. When the water balance is disturbed during dry and arid conditions, the composition releases the absorbed water and the decomposed nitrogenous matter to the soil supplementing its requirement. Insecticidal and fungicidal properties of neem cake inhibits or minimises the attack of common subterranean pests that attack vegetation. Neem cake not only delays the decay or decomposition of coir pith but also prevents pests and other harmful insects from harming the cultivation.

BEST MODE OF CARRYING OUT THE INVENTION

Coir pith is sieved to remove coir fibre and other undesired materials therefrom. Preferably a sieve with 6 mm/4.8 mm screens are used. Conductivity and pH of this coir pith is then tested and if desired the pith is subjected to the washing and drying step. Washing may be either manual or by exposing the same to rains and subsequent drying either in the sun or in an oven. Preferred conductivity is upto 300 mhos and the pH range is 5.0 to 6.8. Moisture limit is up to 20% by weight of moisture.

After sieving and drying the pith is admixed with at least 20% by its weight of powdered neem cake and is then subjected to high pressure in a hydraulic or any other known mechanical press. The composition may be moulded in any desired shape, thickness and size. Large briquettes or discs are made for use in plantation while small coin shaped disc or slabs are made for use in gardens and small scale cultivations.

These moulded compositions may be distributed under the soil before the sowing and planting season, for release of micro-nutrients, fertilizers such as nitrogenous matter, water and pesticides. In course of time, with the help of rain water, the composition decays slowly releasing nutrients and pesticides, the decayed matter acting as soil conditioners. The composition and its action are ecofriendly and environmentally compatible.

This invention relates to a soil conditioner and slow release biopesticidal and fertilizer composition, which comprises at least 20% by weight of powdered neem cake and coir pith having a moisture content of upto 20%, compressed to reduce its volume.

The composition is compressed to reduce its volume in the ratio of 12:1 when small discs or briquettes are made. It is preferred to reduce the volume to 6:1 when larger size units are formed. This composition is ideally suited for desert farming and rain-fed farming conditions.

Obvious equivalents and alterations known to persons skilled in the art are within the scope of this invention.

What is claimed is:

1. A compressed soil conditioner and slow release biopesticidal and fertilizer composition comprising at least 20% by weight of powdered neem seed cake admixed with coir pith of particle size ranging from 4.8 mm to 6 mm, said coir pith having less than 20% by weight of water content and a pH range of 5.0 to 6.8, said composition being compressed to reduce its volume to 12:1.

2. The composition as claimed in claim 1, wherein the composition is reduced to compress its volume in the ratio of 6:1.

3. The composition as claimed in claim 1, wherein said composition is compressed to discs, coins, or briquettes in a hydraulic press having the desired moulds.

* * * * *